United States Patent
Kargar et al.

(10) Patent No.: US 8,848,874 B2
(45) Date of Patent: Sep. 30, 2014

(54) SYSTEM FOR RECOVERING FROM COLLISION OF COMPONENTS OF AN X-RAY IMAGING UNIT

(75) Inventors: Soroosh Kargar, Lake in the Hills, IL (US); Weng Lei, Mount Prospect, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 150 days.

(21) Appl. No.: 13/101,179

(22) Filed: May 5, 2011

(65) Prior Publication Data

US 2012/0069967 A1    Mar. 22, 2012

Related U.S. Application Data

(60) Provisional application No. 61/384,391, filed on Sep. 20, 2010.

(51) Int. Cl.
*A61B 6/00* (2006.01)
*A61B 6/10* (2006.01)

(52) U.S. Cl.
CPC ............ *A61B 6/102* (2013.01); *A61B 6/4441* (2013.01); *A61B 6/54* (2013.01); *A61B 6/586* (2013.01); *A61B 6/547* (2013.01); *A61B 6/545* (2013.01)
USPC ............................ 378/117; 378/196; 378/197

(58) Field of Classification Search
CPC ........ A61B 6/102; A61B 6/4441; A61B 6/54; A61B 6/545; A61B 6/547; A61B 6/586
USPC ................... 378/117, 195, 196, 197, 198
See application file for complete search history.

(56) References Cited

U.S. PATENT DOCUMENTS

| | | | |
|---|---|---|---|
| 7,428,296 B2 | 9/2008 | Bernhardt et al. | |
| 7,837,385 B2 | 11/2010 | Klingenbeck-Regn | |
| 2007/0211861 A1* | 9/2007 | Koertge | 378/117 |
| 2008/0279333 A1 | 11/2008 | Sattler et al. | |
| 2009/0278702 A1 | 11/2009 | Graumann et al. | |
| 2009/0281452 A1 | 11/2009 | Pfister et al. | |
| 2010/0114308 A1 | 5/2010 | Maschke | |

\* cited by examiner

*Primary Examiner* — Glen Kao
(74) *Attorney, Agent, or Firm* — Brennan K Bradley (57) ABSTRACT

A system provides recovery from an X-ray system C-arm and patient table collision. A collision recovery system enables a user to recover from a collision or near collision of movable components of an X-ray imaging system including a movable C-arm hosting an X-ray emitter and detector. The system includes a C-arm position tracking processor for automatically recording C-arm position data indicating a valid stationary position of a C-arm and a path from the valid stationary position to an invalid position of the C-arm enabling retracement of the C-arm along the path to the valid stationary position. A user interface enables a user to initiate retracement of the C-arm along the path to the valid stationary position. A C-arm is movable to retrace the path to the valid stationary position using the recorded C-arm data in response to user command.

20 Claims, 7 Drawing Sheets

| | LAO | CRAN |
|---|---|---|
| starting position (valid) | 0 | 0 |
| path - position 1 | 1 | 1 |
| path - position 2 | 2 | 2 |
| path - position 3 | 3 | 4 |
| path - position 4 | 4 | 5 |
| path - position 5 | 5 | 6.3 |
| path - position 6 | 6 | 7.6 |
| path - position 7 | 7 | 8.9 |
| path - position 8 | 8 | 10.2 |
| path - position 9 | 9 | 11.5 |
| path - position 10 | 10 | 12.8 |
| path - position 11 | 11 | 14.1 |
| path - position 12 | 12 | 15.4 |
| path - position 13 | 13 | 16.7 |
| path - position 14 | 14 | 18 |
| path - position 15 | 15 | 19.3 |
| path - position 16 | 16 | 20.6 |
| path - position 17 | 17 | 21.9 |
| path - position 18 | 18 | 23.2 |
| path - position 19 | 19 | 24.5 |
| path - position 20 | 20 | 25.8 |
| path - position 21 | 21 | 27.1 |
| path - position 22 | 22 | 27.3 |
| path - position 23 | 23 | 28.1 |
| path - position 24 | 24 | 28.4 |
| path - position 25 | 25 | 29.7 |
| path - position 26 | 26 | 31 |
| path - position 27 | 27 | 32.3 |
| path - position 28 | 28 | 33.6 |
| path - position 29 | 29 | 34.9 |
| path - position 30 | 30 | 36.2 |
| path - position 31 | 31 | 37.5 |
| path - position 32 | 32 | 38.8 |
| path - position 33 | 33 | 40.1 |
| path - position 34 - Collision | 34 | 41 |

SYSTEM FOR RECOVERING FROM COLLISION OF COMPONENTS OF AN X-RAY IMAGING UNIT

This is a non-provisional application of provisional application Ser. No. 61/384,391 filed Sep. 20, 2010, by S. Kargar et al.

FIELD OF THE INVENTION

This invention concerns a collision recovery system enabling a user to recover from a collision or near collision of movable components of an X-ray imaging system including a movable C-arm hosting an X-ray emitter and detector.

BACKGROUND OF THE INVENTION

In known X-ray imaging systems, when an X-ray system gets into a collision zone, it is not easy for a user to move the system back to a non-collision zone and proceed to move the C-arm to a desired angle for performing a procedure. A user needs to know how to move the X-ray system elements to get out of the collision zone. This may be difficult to do and a user may have to contact on-site service engineer for help. This is time-consuming and burdensome for physicians and patients, especially so for example, if it occurs during surgery. A system according to invention principles addresses this problem and related problems.

SUMMARY OF THE INVENTION

A system provides recovery from an X-ray system C-arm and patient table collision. A collision recovery system enables a user to recover from a collision or near collision of movable components of an X-ray imaging system including a movable C-arm hosting an X-ray emitter and detector. The system includes a C-arm position tracking processor for automatically recording C-arm position data indicating a valid stationary position of a C-arm and a path from the valid stationary position to an invalid position of the C-arm enabling retracement of the C-arm along the path to the valid stationary position. A user interface enables a user to initiate retracement of the C-arm along the path to the valid stationary position. A C-arm is movable to retrace the path to the valid stationary position using the recorded C-arm data in response to user command.

DETAILED DESCRIPTION OF THE INVENTION

A system provides recovery from an X-ray system C-arm and patient table collision by providing a method to backtrack and retrace C-Arm and/or patient support table positions so that the system returns to a last position prior to a collision or near collision. The system stores data indicating a last valid C-Arm and patient support table position and stores data indicating C-Arm and patient support table movement paths to a current collision position. The system initiates recording C-Arm and table movement in response to a user moving or initiating movement of the C-Arm or table. In case of occurrence of a collision, the system enables a user to retrace a C-Arm and/or patient support table position to a last valid position prior to the collision by reversing the recorded path. A user is able to stop the backtracking movement anytime during the backtracking process and does not need to retrace to the last valid position but can retrace to any position in a backtrack path since a desired position may lie within the backtrack path. The system is usable to recover from a collision caused by moving a user interface button or joystick too fast to move a C-arm to an unwanted position.

Figure 1:
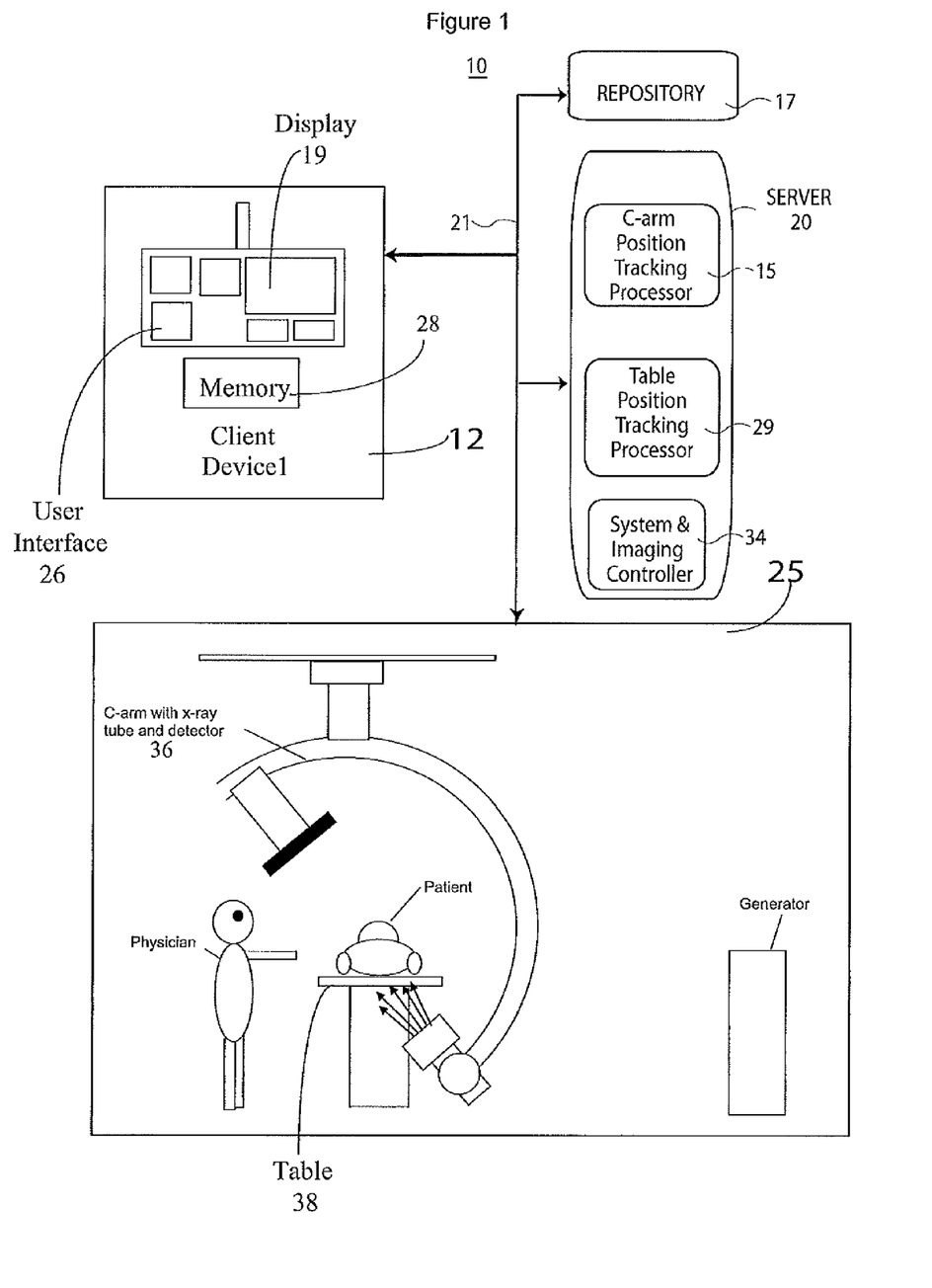
FIG. 1 shows an imaging system including a collision recovery system enabling a user to recover from a collision or near collision of movable components of an X-ray imaging system including a movable C-arm hosting an X-ray emitter and detector, according to invention principles.

FIG. 1 shows imaging and collision recovery system 10 enabling a user to recover from a collision or near collision of movable components of an X-ray imaging system including movable C-arm 36 hosting an X-ray emitter and detector. C-arm 36 is movable in response to a motor drive under user command via user interface 26 but in another embodiment may be manually movable or employ partial power assisted movement. System 10 includes one or more processing devices (e.g., workstations, computers or portable devices such as notebooks, Personal Digital Assistants, phones) 12 that individually include a user interface control device 26 such as a keyboard, mouse, touchscreen, voice data entry and interpretation device, display 19 and memory 28. System 10 also includes at least one repository 17, X-ray imaging modality system 25 (which in an alternative embodiment may comprise an MR (magnetic resonance) or CT scan device, for example) and server 20 intercommunicating via network 21. X-ray modality system 25 provides patient X-ray medical images using C-arm 36, an X-ray radiation source and detector device rotating about patient support table 38 and an associated electrical generator for providing electrical power for the X-ray radiation system. The medical images are generated in response to predetermined user (e.g., physician) specific preferences. At least one repository 17 stores medical image studies for multiple patients in DICOM compatible (or other) data format.

A medical image study individually includes multiple image series of a patient anatomical portion which in turn individually include multiple images. Server 20 includes C-arm position tracking processor 15, patient support table position tracking processor 29 and system and imaging controller 34. Display 19 presents display images comprising a Graphical User Interface (GUI). Imaging controller 34 controls operation of imaging device 25 in response to user commands entered via user interface 26. In alternative arrangements, one or more of the units in server 20 may be located in device 12 or in another device connected to network 21.

Imaging system 25 acquires data representing multiple temporally sequential individual images of vessels of a region of interest of patient anatomy. C-arm position tracking processor 15 automatically records C-arm position data indicating a last valid stationary position of C-arm 36 and a path from the last valid stationary position to an invalid position of C-arm 36 enabling retracement of the C-arm along the path to the last valid stationary position. User interface 26 enables a user to initiate retracement of C-arm 36 along the path to the last valid stationary position. C-arm 36 is movable to retrace the path to the last valid stationary position using the recorded C-arm data in response to user command. System 10 includes movable patient support table 38. Patient support table position tracking processor 29 automatically records table data indicating a last valid stationary position of table 38 and a path from the last valid stationary position of table 38 to an invalid position of the table enabling retracement of the table along the path to the last valid stationary table position.

Figure 2:
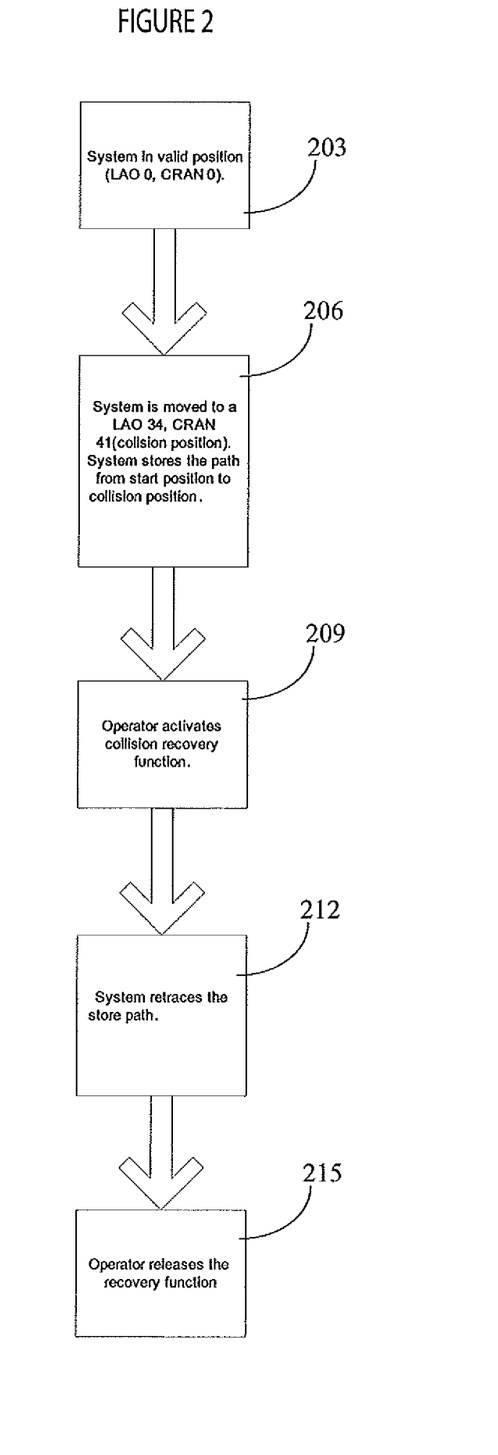
FIG. 2 shows a flowchart of a process used by a collision recovery system, according to invention principles.
Figure 5:
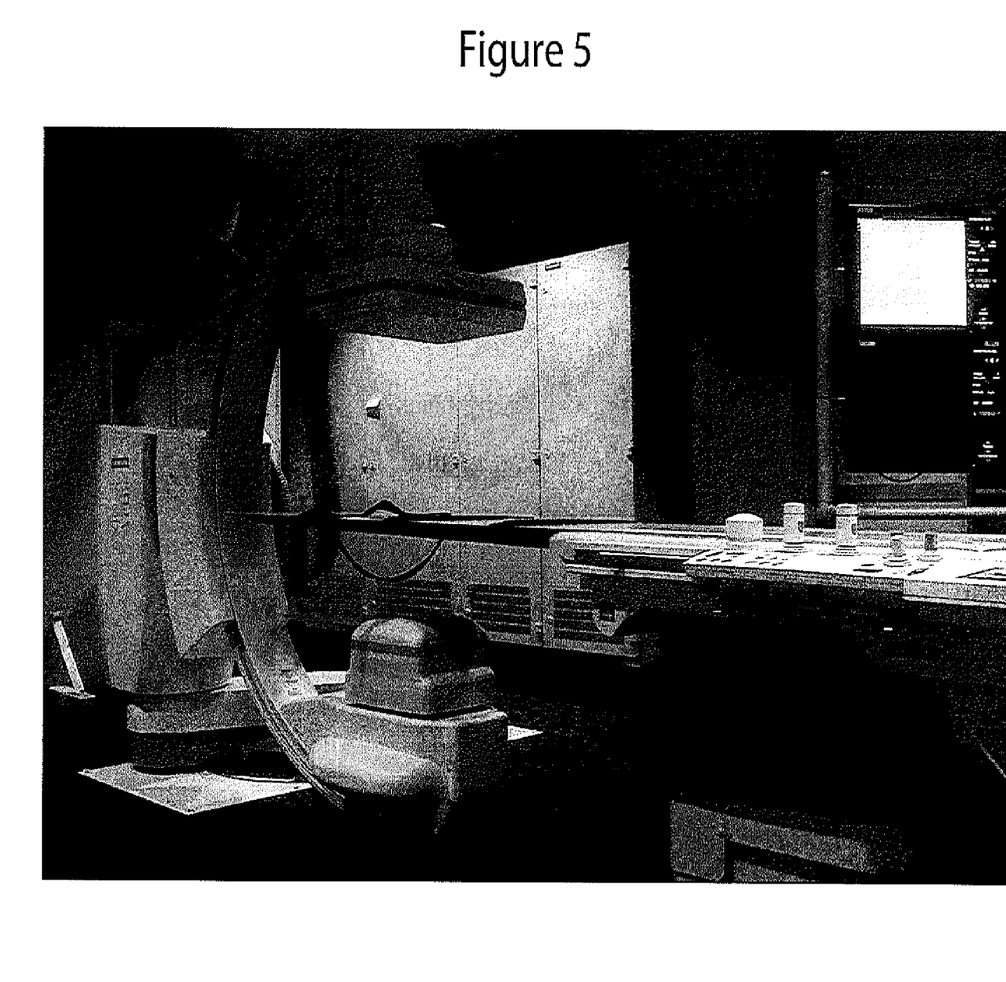
FIG. 5 shows an X-ray imaging system C-arm in a valid start position.
Figure 6:
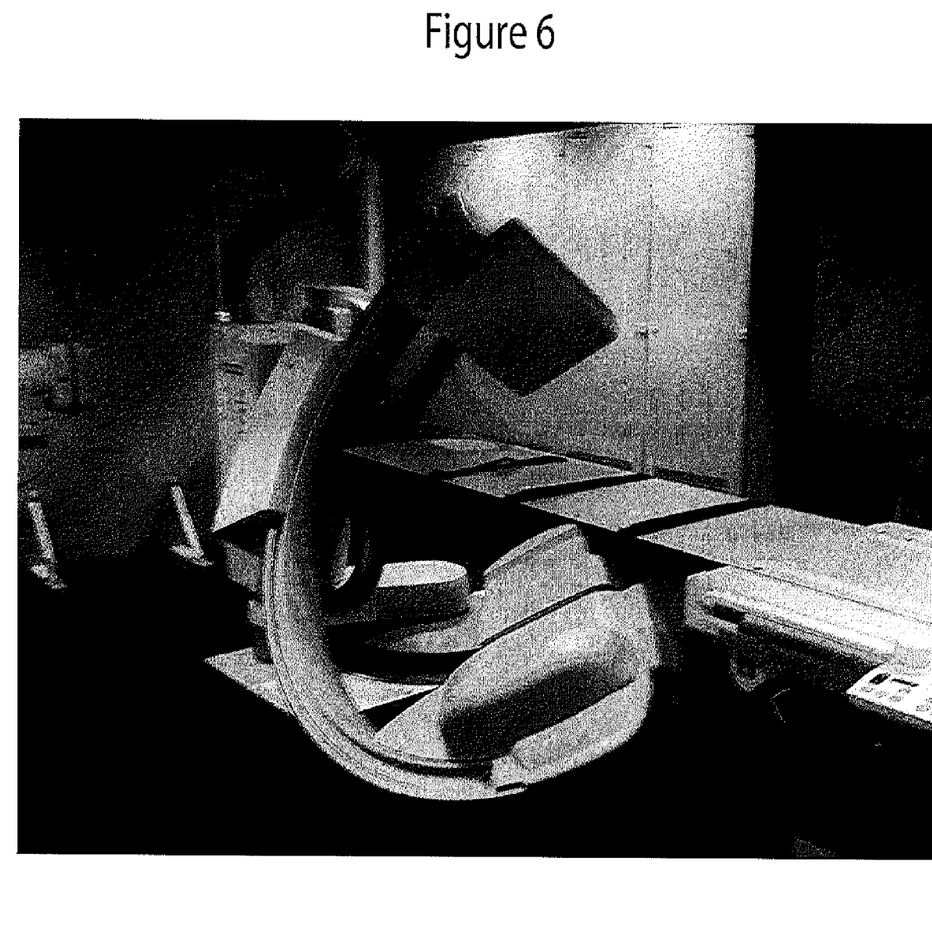
FIG. 6 shows an X-ray imaging system C-arm in a collision position.

FIG. 2 shows a flowchart of a process used by imaging and collision recovery system 10. In step 203 C-arm 36 and patient support table 38 are in valid initial positions. Specifically, C-arm 36 is in an initial position with coordinates LAO 0, CRAN 0. FIG. 5 shows an X-ray imaging system C-arm in a valid start position. Herein LAO/RAO refers to a left/right anterior oblique X-ray radiation detector position, and CRAN/LAUD means cranial/caudal or head/feet viewing orientation with respect to the patient. In step 206, in response to user command via user interface 26, C-arm 36 is moved to a position (LAO 34, CRAN 41) resulting in a collision with patient support table 38. FIG. 6 shows an X-ray imaging system C-arm in a collision position. C-arm position tracking processor 15 automatically records C-arm position data indicating a last valid stationary position of C-arm 36 and a path from the last valid stationary position to an invalid position of C-arm 36 enabling retracement of the C-arm along the path to the last valid stationary position.

Figure 3:
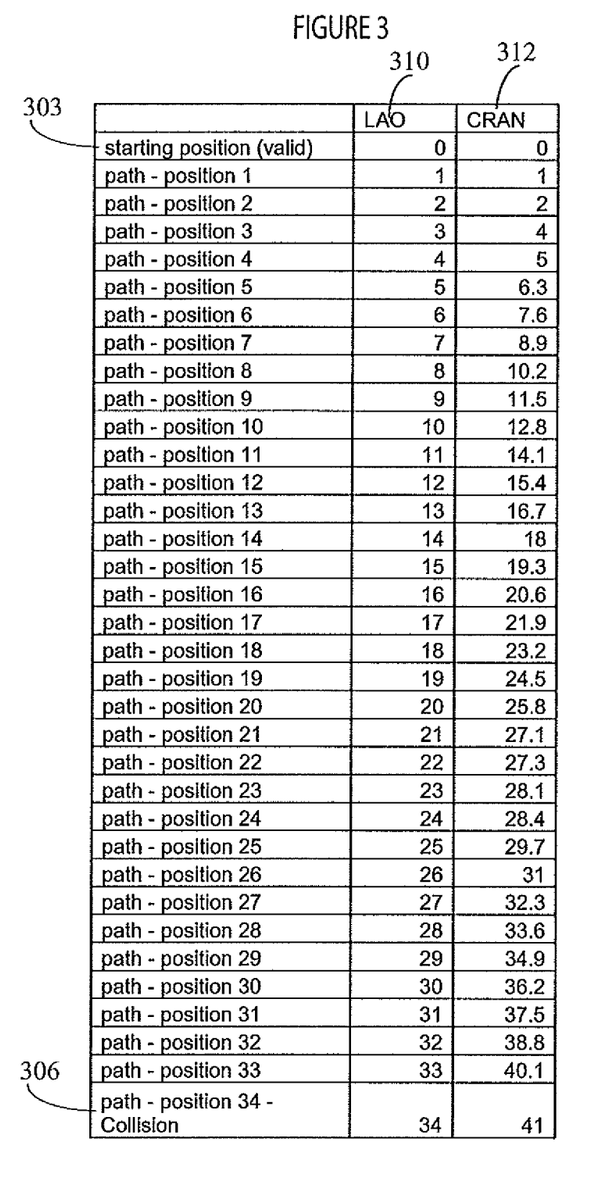
FIG. 3 shows a table indicating a sequence of positions of a C-arm used during an imaging procedure, according to invention principles.

FIG. 3 shows a table of data automatically recorded by C-arm position tracking processor 15. The recorded data shows the initial, valid position 303 and final collision position 306. Positions are identified by LAO and CRAN coordinates of columns 310 and 312 respectively. The recorded data also comprises data indicating the sequence of intermediate positions of C-arm 36 traced during an imaging procedure along the path from position 303 to position 306.

Figure 4:
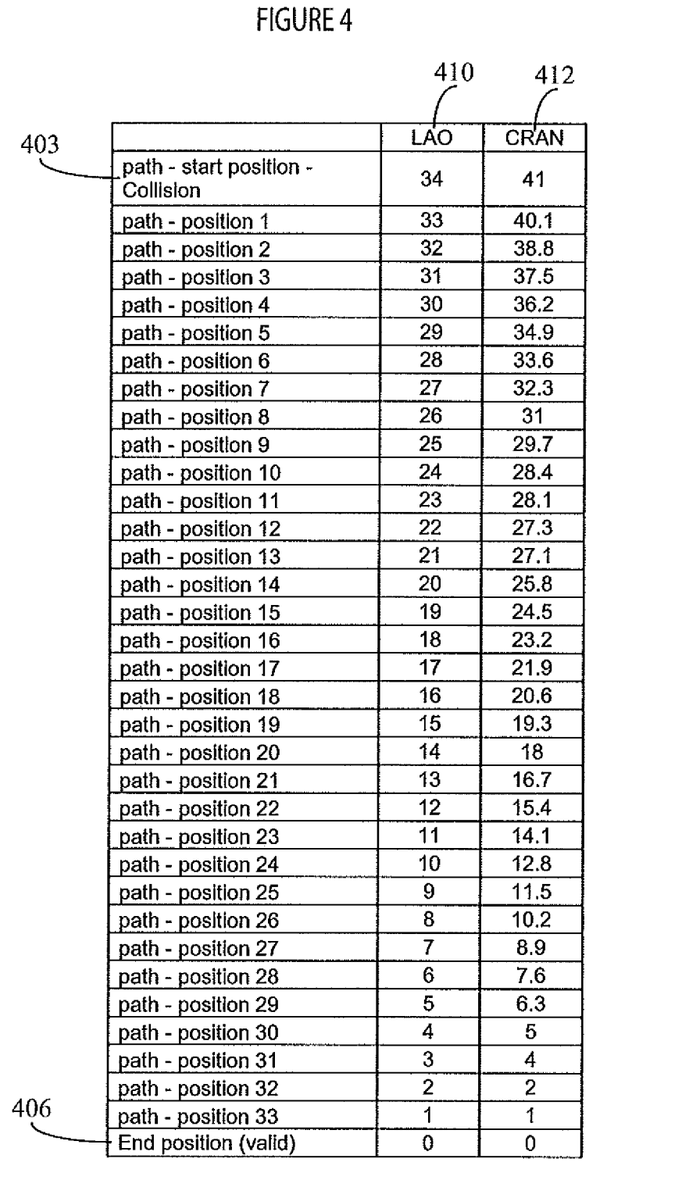
FIG. 4 shows a table recording a sequence of positions for retracing movement of a C-arm during an imaging procedure, according to invention principles.

In step 209 (FIG. 2), a user activates a collision recovery function and C-arm 36 in step 212 is automatically driven along a path retracing the original path shown in FIG. 3. C-arm position tracking processor 15 automatically generates the retracement path coordinate data of the FIG. 4 table that records a sequence of positions for retracing movement of a C-arm during an imaging procedure. C-arm position tracking processor 15 automatically generates the retracement path coordinate data of the FIG. 4 table using the original path data shown in FIG. 3 by in one embodiment reversing the order of the original tracked path coordinates to provide the retracement path coordinate sequence illustrated in FIG. 4, for example. The generated data shows the initial, collision position 403 and final valid position 406. Positions are identified by LAO and CRAN coordinates of columns 410 and 412 respectively. The generated data also comprises data indicating the sequence of intermediate retracement positions of C-arm 36 traced during an imaging procedure along the path from position 403 to position 406. In step 215, a user terminates use of the collision recovery system.

System 10 provides a method of C-arm and table collision recovery for an X-ray angiography system, for example. System 10 stores multiple previous retracement positions and the number, increment and type (e.g. type of position coordinates used) of stored positions is configurable by a user. Further, a physician may prefer to recover from a collision position manually using user interface 26. System 10 is advantageously configurable for manual or automatic path retracement to recover from a collision position.

Figure 7:
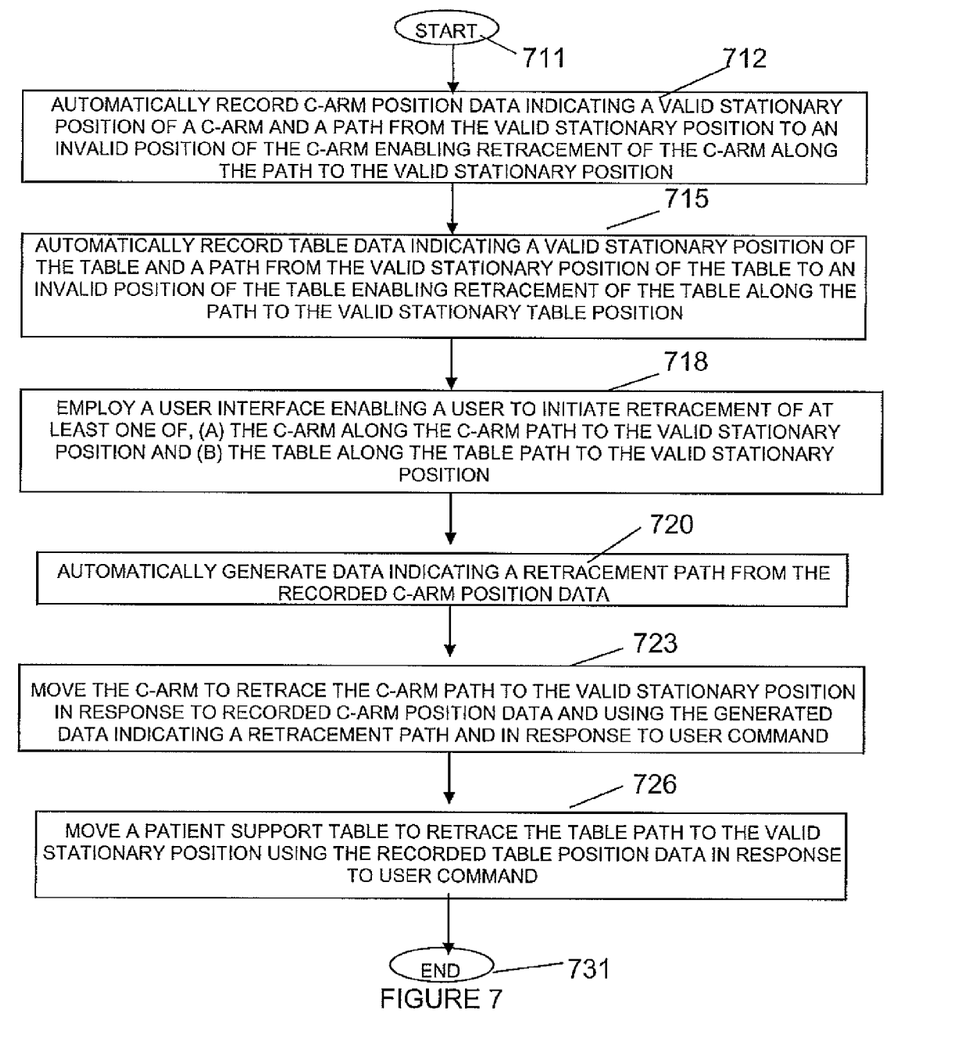
FIG. 7 shows a flowchart of a process used by a collision recovery system enabling a user to recover from a collision or near collision of movable components of an X-ray imaging system, according to invention principles.

FIG. 7 shows a flowchart of a process used by imaging and collision recovery system 10 (FIG. 1) enabling a user to recover from a collision or near collision of movable components of an X-ray imaging system. In step 712 following the start at step 711, C-arm position tracking processor 15 automatically records C-arm position data indicating a valid stationary position of C-arm 36 and a path from the valid stationary position to an invalid position of the C-arm enabling retracement of the C-arm along the path to the valid stationary position. Specifically, C-arm position tracking processor 15 automatically records C-arm position data indicating a sequence of valid stationary positions of a C-arm and a path through the sequence of valid stationary positions to an invalid position of the C-arm enabling retracement of the C-arm along the path to a point within the path. C-arm 36 is automatically movable, manually movable or movable manually with power assistance to retrace the path to a user selected point along the path using the recorded C-arm data in response to user command.

In step 715, patient support table position tracking processor 29 automatically records table data indicating a valid stationary position of table 38 and a path from the valid stationary position of the table to an invalid position of the table enabling retracement of the table along the path to the valid stationary table position in response to user command. Table 38 is automatically movable, manually movable or movable manually with power assistance. User interface 26 enables a user to initiate retracement of C-arm 36 along the path to a user selected point along the path and enables a user to initiate retracement of table 38 along the path to the valid stationary table position. User interface 26 enables a user to configure the number of valid stationary positions.

In step 718, a user initiates, via user interface 26, retracement of at least one of, (a) the C-arm along the C-arm path to the valid stationary position and (b) the table along the table path to the valid stationary position. C-arm position tracking processor 15 in step 720 automatically generates data indicating a retracement path from the recorded C-arm position data by reversing the order of original tracked path coordinates to provide a retracement path coordinate sequence. In step 723, C-arm 36 is moved to retrace the path to the valid stationary position in response to the recorded C-arm position data and using the generated data indicating a retracement path and in response to user command. In step 726, patient support table 38 is moved to retrace the table path to the valid stationary position using the recorded table data in response to user command. The process of FIG. 7 terminates at step 731.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouth, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-7 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system enables a user to retrace a C-Arm and/or patient support table position to a last valid position prior to a collision by reversing the recorded path and a user is able to retrace to a selected position within a backtrack path. Further, the processes and applications may, in alternative embodiments, be located on one or more (e.g., distributed) processing devices on a network linking the units of FIG. 1. Any of the functions and steps provided in FIGS. 1-7 may be implemented in hardware, software or a combination of both.

What is claimed is:

1. A collision recovery system for an X-ray imaging system including a movable C-arm coupled to an X-ray emitter and an X-ray detector, comprising:

a C-arm position tracking processor for automatically recording C-arm position data indicating a last valid stationary position of a C-arm and a path from the last valid stationary position to an invalid position of the C-arm;

a user interface to receive a command from a user to initiate retracement of the C-arm along the path to the last valid stationary position; and a C-arm movable to, in response to the command, retrace the path and stop at the last valid stationary position until a next command is received from the user based on the recorded C-arm position data.

2. A system according to claim 1, wherein
said X-ray imaging system includes a movable patient support table and including,
a patient support table position tracking processor for automatically recording table data indicating a last valid stationary position of the table and a path from the last valid stationary position of the table to an invalid position of the table.

3. A system according to claim 2, wherein
said user interface is to receive a command from the user to initiate retracement of the table along the path to the last valid stationary position of the table; and
said patient support table is movable to retrace the path to the last valid stationary position of the table using the recorded table data in response to the command from the user to initiate retracement of the table along the path to the last valid stationary position of the table.

4. A system according to claim 2, wherein
said table is automatically movable.

5. A system according to claim 2, wherein
said table is at least one of, (a) manually movable and (b) movable manually with power assistance.

6. A system according to claim 1, wherein
said C-arm is automatically movable.

7. A system according to claim 1, wherein
said C-arm is at least one of, (a) manually movable and (b) movable manually with power assistance.

8. A system according to claim 1, wherein
said user interface enables a user to initiate retracement of the C-arm along the path to a user selected point along the path and
said C-arm is movable to retrace the path to a user selected point along the path using the recorded C-arm data in response to user command.

9. A system according to claim 1, wherein
said C-arm position tracking processor automatically records C-arm position data indicating a sequence of valid stationary positions of a C-arm and a path through the sequence of valid stationary positions to an invalid position of the C-arm enabling retracement of the C-arm along the path to a point within the path.

10. A system according to claim 1, wherein
said user interface enables a user to configure a number of valid stationary positions.

11. A system according to claim 1, wherein
said C-arm position tracking processor automatically generates data indicating a retracement path from the recorded C-arm position data and
said C-arm is moved to retrace the path to the valid stationary position using the generated data indicating a retracement path.

12. A system according to claim 11, wherein
said C-arm position tracking processor automatically generates data indicating said retracement path by reversing the order of original tracked path coordinates to provide a retracement path coordinate sequence.

13. A collision recovery system for an X-ray imaging system including a movable patient support table and a movable C-arm coupled to an X-ray emitter and an X-ray detector, comprising:
a C-arm position tracking processor for automatically recording C-arm position data indicating a last valid stationary position of a C-arm and a path from the last valid stationary position of the C-arm to an invalid position of the C-arm;
a patient support table position tracking processor for automatically recording table data indicating a last valid stationary position of the table and a path from the last valid stationary position of the table to an invalid position of the table;
a user interface to receive a command from a user to initiate retracement of at least one of, (a) the C-arm along the C-arm path to the last valid stationary position of the C-arm and (b) the table along the table path to the last valid stationary position of the table;
a C-arm movable, in response to the command, to retrace the C-arm path and to stop at the last valid stationary position of the C-arm until a next command is received from the user based on the recorded C-arm data; and
a patient support table movable, in response to the command, to retrace the table path and to stop at the last valid stationary position of the table until the next command is received from the user based on the recorded table data.

14. A system according to claim 13, wherein
said C-arm position tracking processor automatically records C-arm position data indicating a sequence of valid stationary positions of the C-arm and a sequence of valid stationary positions to the invalid position of the C-arm, enabling retracement of the C-arm along the path to a position within the path.

15. A system according to claim 13, wherein
said user interface enables a user to configure a number of valid stationary positions of the C-arm.

16. A method for an X-ray imaging system including a movable C-arm coupled to an X-ray emitter and an X-ray detector, comprising:
automatically recording C-arm position data indicating a last valid stationary position of a C-arm and a path from the last valid stationary position to an invalid position of the C-arm;
receiving a command from a user to initiate retracement of the C-arm along the path to the last valid stationary position; and
moving the C-arm, in response to the command, to retrace the path and to stop at the last valid stationary position until a next command is received from the user based on the recorded C-arm position data.

17. A method according to claim 16, wherein
said X-ray imaging system includes a movable patient support table and including the activity of,
automatically recording table data indicating a last valid stationary position of the table and a path from the last valid stationary position of the table to an invalid position of the table.

18. A method according to claim 17, further comprising:
receiving a command to initiate retracement of the table along the path to the last valid stationary position of the table, and
moving said patient support table to retrace the path to the last valid stationary position of the table using the recorded table data in response to the second command to initiate retracement of the table along the path to the last valid stationary position of the table.

19. A method according to claim 16, further comprising:
automatically generating data indicating a retracement path from the recorded C-arm position data and
moving said C-arm to retrace the path to the last valid stationary position using the generated data indicating the retracement path.

20. A method according to claim 16, further comprising:
automatically generating data indicating a retracement path from the recorded C-arm position data by reversing the order of original tracked path coordinates to provide a retracement path coordinate sequence.

* * * * *